United States Patent [19]

Daigle et al.

[11] Patent Number: 5,460,187
[45] Date of Patent: Oct. 24, 1995

[54] FLUOROSCOPICALLY VIEWABLE GUIDEWIRE

[75] Inventors: James B. Daigle, Worcester; Richard M. DeMello, Acton; Bruce W. Flight, Melrose, all of Mass.

[73] Assignee: Boston Scientific Corp., Natick, Mass.

[21] Appl. No.: 270,034

[22] Filed: Jul. 1, 1994

[51] Int. Cl.⁶ ........................................................ A61B 5/00
[52] U.S. Cl. ................................................ 123/772; 128/697
[58] Field of Search ...................................... 128/657, 772; 604/164, 170, 280, 282

[56] References Cited

U.S. PATENT DOCUMENTS

| Re. 34,695 | 8/1994 | Mar et al. ............................ 128/772 |
| 4,020,829 | 5/1977 | Willson et al. ...................... 128/657 |
| 4,748,986 | 6/1988 | Morrison et al. .................... 128/772 |
| 4,815,478 | 3/1989 | Buchbinder et al. ................. 128/772 |
| 4,922,924 | 5/1990 | Gambale et al. ................... 128/657 X |
| 4,953,553 | 9/1990 | Tremulis ............................ 128/772 X |

*Primary Examiner*—Sam Rimell

[57] ABSTRACT

A guidewire adapted to be inserted into a vascular vessel or into a catheter that is to be inserted into a vascular vessel or the like. The guidewire comprises a coil of flexible radiotransparent wire having a proximal section and a distal section. The proximal section is formed of a coil of wire having abutting turns and distal section is formed by the same coil of wire with the turns of wire being spaced from each other. A layer of radiopaque material of predetermined length is disposed in a predetermined location on the distal section, the interior of the layer being interstitially disposed within the outer surface of the coil. A hemispherical tip is disposed at the distal end of the distal section. A small braze is made at the juncture between the proximal section and the distal section to prevent spreading of the coils from the abutting relationship in the proximal end of said guidewire.

10 Claims, 1 Drawing Sheet

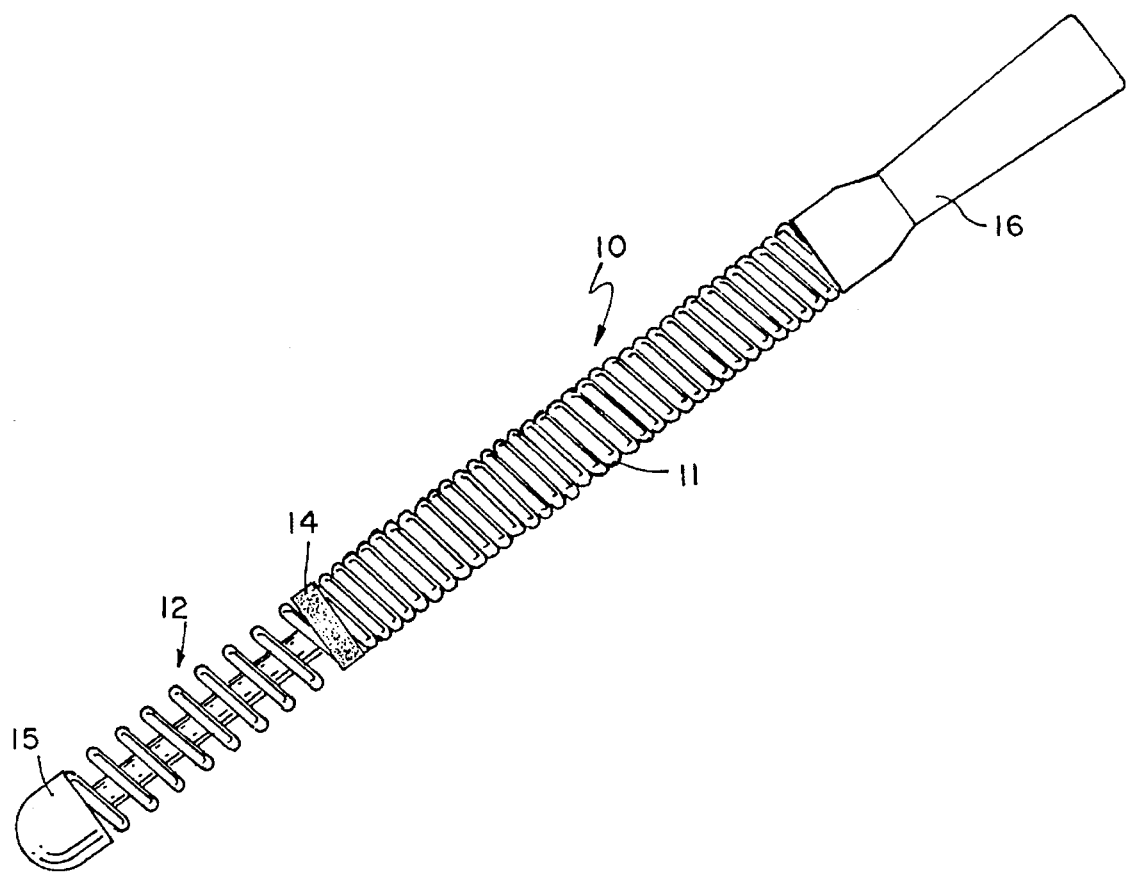

FLUOROSCOPICALLY VIEWABLE GUIDEWIRE

FIELD OF THE INVENTION

The present invention relates to an improved guidewire for insertion into a vascular vessel or into a catheter that is to be inserted into a vascular vessel or the like. Specifically the present invention relates to a coiled guidewire which comprises a proximal section and a distal section. A coating of gold or platinum is disposed on the distal section of the guidewire and is formed such that it is disposed in a predetermined location and is of predetermined length. The interior of the coating is not merely disposed on the substrate but is interstitially disposed within the outer surface of the substrate. The guidewire can be inserted into the vessel and can enable a physician to identify the magnitude and location of a target site through radiography.

DESCRIPTION OF THE PRIOR ART

Guidewires formed of coiled wire are well known in the art and the disposition of core wires within the guidewire is also known. For example, the U.S. Pat. Nos. to Daigle et al., 5,253,653; Claude, 5,084,022; Gambale et al., 5,060,660, are illustrative of coiled guidewires. Mechanisms to define radiopacity in a guidewire to define dark images on coiled guidewires are also known to the art in, for example, Gambale et al., 5,144,959, and Daigle et al., 5,253,653.

SUMMARY OF THE INVENTION

According to the present invention we have invented a novel flexible, shapable guidewire which can be used by itself or within a catheter sleeve. The guidewire of our invention has a radiopaque tip disposed in its distal end. While coatings have previously been disposed upon guidewire tips to make them radiopaque for radiographic identification of their location, we have discovered when such materials are merely coated upon guidewires they tend to have less than satisfactory adhesion and processes for coating the substrates can involve the use of deleterious chemicals. Such markers have conventionally been made of silver, gold, platinum, tantalum or other radiopaque biocompatible materials.

According to the present invention the radiopaque metal is applied to a stainless steel coil by means of an ion beam deposition process. In the ion beam deposition process the coating metal is implanted beneath the surface of the substrate to effectuate a bond. Such implantation is provided without the use of chemicals and thus eliminates certain hazards in the product associated with residual chemicals in the product when using traditional electrochemical deposition processes. According to the invention the coil has a substrate of stainless steel and an outer layer which is a combination of the stainless steel and the ion implanted coating disposed thereon. On top of the ion implanted layer is a layer of the radiopaque material itself.

Such deposition methods eliminate the problems associated with a guidewire that is stiff at the joint between radiopaque coils and radiotransparent coils since there is no need to braze, solder or adhesively attach multiple components. Moreover the problem related to the joint failing is also eliminated.

The guidewire construction of the present invention enables a single length of coil to display varying degrees of radiopacity traditionally associated with an assembly of different materials. The coil's performance is not compromised due to stiffness created by component attachment joints. The surface enhancement of the device is by means of an ion beam deposition of dense materials provides a denser and less porous deposition of these materials over known electrochemical deposition methods. Thus radiopacity can be enhanced without the introduction of deleterious chemicals. Quite importantly, with the use of an expanded coil in the distal section of the guidewire the entire coil, both inside and out, can be coated with the radiopaque materials.

The guidewire of the present invention is adapted to be inserted into a vascular vessel or into a catheter that is to be inserted into a vascular vessel or the like. The guidewire includes a coil of flexible radiotransparent wire which has a proximal and a distal section. The proximal section is formed of a coil of wire having abutting turns and the distal section being formed by the same coil of wire with the turns of wire being spaced from each other. A layer of radiopaque material of predetermined length disposed in a predetermined location on the distal section, the interior of the layer being interstitially disposed within the outer surface of said coil. A tip is disposed at the distal end of said distal section.

The many other features, objects and advantages of the present invention can become apparent from and are set out in more detail in the accompanying drawing and following descriptions of the best mode of carrying out the invention.

BRIEF DESCRIPTION OF THE DRAWING

The Figure is a side elevational view of a guidewire according to the present invention.

DESCRIPTION OF THE PREFERRED EMBODIMENTS

Referring now to the Figure a coiled guidewire 10 is formed of a proximal section 11 and a distal section 12. A braze 14 is disposed between the proximal section 11 and the distal section 12. The two sections are formed of a single coil of stainless steel wire having a diameter between about 0.010 and 0.040 inches in diameter and formed of wire having a diameter from 0.001 to 0.01 inches. The proximal section 11 of the coil is tightly wound with turns touching and the distal section 12 being open wound with turns not touching. The guidewire 10 terminates in a hemispherical-shaped tip 15 formed by welding, soldering, or brazing.

The distal section of the guidewire is generally between about one and five centimeters and the entire length of the coil section is between about fifteen and fifty centimeters, although the coil could extend over the full length of the guidewire. The diameter of the tip 15 is about the same as the diameter of the coiled guidewire 10.

The braze 14 is disposed between the proximal section 11 and the distal section 12 to prevent the coil in the proximal section 11 from stretching as the guidewire is removed from the vascular conduit in which it is inserted, and also to aid in guidewire torque transmission. No significant stiffness is contributed by the braze.

The proximal end of the proximal section 11 has a retaining device 16 disposed thereon. The retaining device enables the person operating the guidewire to turn and orient the guidewire within the vascular conduit.

A core wire 5 is disposed within the guidewire 10. The core wire 5 is necked down or tapered from a larger diameter to a smaller diameter at the braze 14 the diameter of the core wire inside the distal section 12 is between about 0.002 to 0.006 inch and within the proximal section 10 is about 0.020 inch. The tip of the core wire 5 is disposed within the tip 15. The core wire provides stability to the guidewire during its use.

The radiopaque material is disposed on the distal section 12 by conventional ion implantation processes. A predetermined length of the distal section of the guidewire is impregnated with gold or other radiopaque material so as to create a radiopaque distal section on an otherwise radiolucent coil. This is accomplished under vacuum whereby an ion beam impinging on the coil surface causes the coil to give off material creating an irregular substrate of microscopic depth. A second ion beam, with vaporized radiopaque material in its path, then impinges on the coil surface filling the irregular substrate and continues to deposit radiopaque material to a controlled desired thickness.

It is apparent that modifications and changes can be made within the spirit and scope of the present invention but it is our intention, however, only to be limited by the scope of the appended claims.

As our invention we claim:

1. A guidewire adapted to be inserted into a vascular vessel or into a catheter that is to be inserted into a vascular vessel or the like, said guidewire comprising:

a coil of flexible radiotransparent metal wire, said coil having a proximal section and a distal section, said proximal section being formed of a coil of wire having abutting turns, said distal section being formed by the same coil of wire with the turns of wire being spaced from each other;

a coating of radiopaque metal of predetermined length disposed in a predetermined location on said distal section, the interior of said coating forming an intermediate layer comprising said substrate and said coating, said intermediate layer being interstitially disposed within the outer surface of said coil and beneath said coating;

a tip disposed at the distal end of said distal section;

means disposed at the juncture between the proximal section and the distal section to prevent spreading of the coils from the abutting relationship in the proximal end of said guidewire.

2. The guidewire according to claim 1 further including a core wire axially disposed within said guidewire, the diameter of said core wire being less in said distal section than in said proximal section, said core wire being formed of a radiotransparent metal.

3. The guidewire according to claim 2 wherein the diameter of the core wire in the distal section is less than about half the diameter of the core wire in the proximal section.

4. The guidewire according to claim 1 wherein said guidewire is formed of stainless steel or nickel titanium alloys and said coating is formed of gold or platinum.

5. The guidewire according to claim 1 wherein the coating has a thickness between about less than 0.0001 and 0.0006 inches.

6. The guidewire according to claim 1 wherein said coating is disposed on both the inside and the outside of the coils of the guidewire.

7. The guidewire according to claim 1 wherein the diameter of the coil is between about 0.006 to 0.040 inches.

8. The guidewire according to claim 7 wherein the diameter of the wire forming the coil is between about 0.0010 and 0.010 inches.

9. The guidewire according to claim 1 wherein coils in the distal section are spaced apart and not in contact with each other.

10. A guidewire adapted to be inserted into a vascular vessel or into a catheter that is to be inserted into a vascular vessel or the like, said guidewire comprising:

a coil of flexible radiotransparent metal wire, said coil having a proximal section and a distal section, said proximal section being formed of a coil of wire having abutting turns, said distal section being formed by the same coil of wire with the turns of wire being spaced from each other;

a coating of radiopaque metal formed by ion implantation of said coil of wire, the interior of said coating being interstitially disposed within the outer surface of said coil, said coating being of predetermined length disposed in a predetermined location on said distal section;

a tip disposed at the distal end of said distal section;

means disposed at the juncture between the proximal section and the distal section to prevent spreading of the coils from the abutting relationship in the proximal end of said guidewire.

* * * * *